United States Patent [19]

Livingston

[11] Patent Number: 5,316,014
[45] Date of Patent: May 31, 1994

[54] BIOPSY LOCATOR AND GUIDE

[75] Inventor: Troy W. Livingston, Northbrook, Ill.

[73] Assignee: Livingston Products, Inc., Wheeling, Ill.

[21] Appl. No.: 831,215

[22] Filed: Feb. 7, 1992

[51] Int. Cl.$^5$ ............................................. A61B 10/00
[52] U.S. Cl. ................................... 128/754; 128/665; 128/653.1; 606/130; 378/37; 378/706
[58] Field of Search ............... 128/754, 753, 752, 751, 128/749, 664, 665, 653.1, 662.05, 663.01; 606/130; 604/116; 378/37, 204, 205, 206; 359/618, 629; 356/121, 122, 125, 153, 401, 256; 353/34, 82, 87, 94

[56] References Cited

U.S. PATENT DOCUMENTS

| | | | |
|---|---|---|---|
| 4,563,768 | 1/1986 | Read et al. | 378/37 |
| 4,651,732 | 3/1987 | Frederick | 606/130 |
| 4,750,487 | 6/1988 | Zanetti | 606/130 |
| 4,821,727 | 4/1989 | Levene et al. | 128/653 |
| 4,836,671 | 6/1989 | Bautista | 356/1 |
| 5,031,203 | 7/1991 | Trecha | 378/205 |
| 5,040,872 | 8/1991 | Steinle | 359/638 |
| 5,053,042 | 10/1991 | Bidwell | 606/130 |
| 5,056,523 | 10/1991 | Hotchkiss, Jr. et al. | 128/753 R |
| 5,078,142 | 1/1992 | Siczek et al. | 128/653.1 |
| 5,083,570 | 1/1992 | Mosby | 128/751 |
| 5,107,843 | 4/1992 | Aarnio et al. | 128/662.05 |
| 5,155,623 | 10/1992 | Miller et al. | 359/495 |
| 5,157,533 | 10/1992 | Hanamoto | 359/204 |

FOREIGN PATENT DOCUMENTS

2384481  11/1978  France ............................ 606/130

Primary Examiner—Stephen C. Pellegrino
Assistant Examiner—Guy V. Tucker
Attorney, Agent, or Firm—Fitch, Even, Tabin & Flannery

[57] ABSTRACT

Method and apparatus for locating and guiding a biopsy needle with respect to an X-rayed specimen having a tumor to be engaged by the needle. Intersecting laser beams are utilized to mark the location of the tumor and to guide the biopsy needle in a vertical path. The laser beam source is movable in orthogonal paths while compensating means redirect the beams to maintain them within a target area.

12 Claims, 7 Drawing Sheets

BIOPSY LOCATOR AND GUIDE

The present invention relates to an instrument for use in guiding and directing a biopsy needle in obtaining a specimen of human tissue, and more specifically relates to apparatus for projecting a pair of laser beams to define the location of an internal lesion and guide a biopsy needle to the lesion.

BACKGROUND OF THE INVENTION

In recent years the public has become very aware of the importance of X-ray examination of women's breasts in the control and cure of breast cancer. The early detection of cancerous tumors is recognized as significantly improving the chances of successful treatment. As a consequence, women of a certain age or genealogical background are subject to X-ray examination of their breasts at frequent intervals. Such examination often detects tumors or lesions which are of a questionable character, it being impossible to determine from the X-ray whether the tumor or lesion is malignant or benign. In such situations, it is normal to take a specimen or biopsy of the tumor or lesion to permit a careful examination of the abnormal tissue.

The most common means of taking a biopsy of a tumor or lesion in a woman's breast is by using an elongated needle which may be inserted with a rotary movement to cut a core sample of tissue in the area of the tumor or lesion. The needle is equipped with suction means to aid in extracting the cylindrical section of tissue. Since the current trend is toward early detection through frequent examination, the tumor or lesion which is to be checked through the biopsy is often very small and barely discernable on the X-ray. With the tumor or lesion often being well below the skin surface, it is extremely difficult to insert the biopsy needle with sufficient accuracy to engage and sample the area of tissue that is of interest and requires further testing.

In the presently used procedure, the breast of the patient is compressed against a horizontal surface below which the X-ray film is positioned. The compressing member is placed above the breast, clamping it against the surface, leaving a panel of skin exposed through a rectangular opening which has indicia on the sides of the opening to aid in establishing the location of the tumor discovered on the X-ray. By establishing the coordinates of the location of the tumor from the X-ray, a mark is placed on the location on the exposed skin using the indicia beside the opening to show where the biopsy needle should be inserted. An additional X-ray is taken to show the depth of the tumor so that the needle may be inserted and the specimen taken at the proper depth below the skin surface. After a biopsy specimen has been taken, another X-ray is taken to assure that the biopsy specimen is from the suspected tissue.

Because of the limited size of the tissue to be sampled and the possible errors in correlating the location of the needle insertion with the location of the tumor as shown on the X-ray, it is not unusual for many needle insertions to be required before achieving the proper location of the needle with respect to the tumor. The procedure causes considerable pain and discomfort and the prolongation resulting from the techniques employed suggest that improved techniques are required.

One attempt at locating the biopsy needle more precisely with respect to an X-ray picture of a tumor has involved the use of movable cross wires to create a shadow produced by an incandescent lamp to locate the needle insertion point on the skin. This technique has not proven to be particularly helpful, since the shadow image of the wires was not sharp enough to give a precise location and the normal ambient light in the area was usually too high to permit good visibility of the shadow image of the wires.

Another approach involved use of a laser dot which was projected in from the side to spot the needle insertion location on the skin. The angle at which the laser beam was projected tended to introduce errors since any deflection of the skin would cause the laser spot to shift location.

Another problem associated with the biopsy is the difficulty of inserting the needle in a direction perpendicular to the horizontal support surface. The selected location on the skin is intended to be directly over the tumor, so the needle must be inserted vertically if it is to engage the tumor. However, the biopsy needle is designed to be rotated as it is inserted. Otherwise, the sharp angled end on the needle will tend to deflect the path of the needle to one side as it is inserted. Experience has revealed that it is very difficult to rotate the biopsy needle and maintain its vertical orientation as it is inserted. Accordingly, it would be desirable to provide means for locating the insertion point for a biopsy needle and for guiding the needle to maintain its vertical position as it is inserted.

SUMMARY OF THE INVENTION

The present invention involves method and apparatus for obtaining a biopsy specimen after having identified a tumor or lesion through X-ray examination. The X-ray machine in connection with which the invention is used has an X-ray head supported above a specimen supporting platform with means provided to immobilize or clamp the specimen to be examined, as for example a woman's breast, against the platform An X-ray film is disposed on the platform so that the X-rays radiated from the head pass through the specimen and provide an image of the specimen on the film. When a possible cancerous tumor or lesion is noted in the X-ray, it often becomes desirable to take a biopsy for further testing to ascertain the nature of the tumor. In order to take the biopsy, it is necessary to identify on the patient's skin exactly where the biopsy needle should be inserted to engage the tumor or lesion observed on the X-ray.

In the method and apparatus of the present invention, a pair of laser sources are detachably mounted between the X-ray head and the specimen platform to provide two aligned intersecting laser beams that are directed along the same common axis as the radiated X-rays. The laser beams are focused to be visible on the surface of the X-rayed specimen as a pair of lines which intersect at 90° to each other. The laser sources are mounted on a carriage which is movable along one path parallel to one of the lines and along another path parallel to the other line. Thus, by moving the carriage along either of two mutually perpendicular paths, the location of the intersection of the lines formed by the laser beams may be moved to any desired location. The clamping means or plate, which overlies the specimen platform and clamps the specimen, is formed with a rectangular opening in which a portion of the specimen is exposed. The specimen is disposed so that the tumor or lesion to be biopsied lies under the skin which is exposed through the opening in the clamping means. In order to insert the biopsy needle accurately, it is necessary to provide a marking or indication on the exposed skin as to where the biopsy needle should be inserted to engage the tumor or lesion indicated by the X-ray. A scale is used to establish the coordinates of the tumor location in the clamping means opening. These coordinates are then used to position the laser beam lines intersecting at the location on the skin above the tumor.

The laser beams are generated by diode lasers generating an oval dot which is directed through a cylindrical lens to expand the beam to form a line which is reflected from a mirror onto the specimen. The beams as they are directed toward the specimen are substantially coaxial, appearing to emanate from a single source. The laser source closest to the specimen is reflected by a beam splitter which only reflects 50% of the impinging beam. The beam from the laser source more remote from the specimen is first reflect by a mirror and that beam is directed through the beam splitter toward the specimen, with 50% of the beam passing directly through the beam splitter and to the specimen and 50% being reflected. This results in the two beams being coaxial and intersecting as they pass from the beam splitter to the specimen. The laser head containing the two laser sources is detachably mounted directly in line with the X-ray head so that the laser beams engage the specimen along the same line or axis as the X-rays. This alignment eliminates any errors in using the laser beams as a locating or indicating means for the tumors which were located from the X-ray image.

One of the serious problems in using laser beams to target or locate a position on the skin for inserting a biopsy needle is the fact that the laser beams may reflect from the clamping means into the eyes of the person using the instrument or the patient on whom it is being used. If the lasers used for locating the tumor in the specimen are reflected from the clamping means into the eyes of the patient or doctor, the apparatus would not be considered acceptable for this type of use. Accordingly, the laser beams are provided with compensation means that redirects the beams as the laser supporting carriage is traversed so that the locating lines on the specimen remain on the exposed portion of the skin within the opening in the clamping means. Cams are provided so that as the carriage traverses in either of the two orthogonal directions, the mirror and the beam splitter are adjusted to maintain the centering of the laser lines within the opening in the clamping means.

The elements of the laser sources, including the diode lasers and the lenses as well as the mirror and beam splitter, are all mounted in a single Delrin block which forms the major portion of the movable carriage. The block provides a vibration-free and dimensionally precise means of mounting the laser sources and the adjustable mirror and beam splitter. Drilled pockets receive the diode lasers and the cylindrical lenses. Drilled holes are provided to receive axles that pivot the mirror and beam splitter and to receive guide rods for mounting the block for transverse movement.

The carriage providing the movable mounting for the laser sources includes an inverted U-shaped frame mounted for what will be termed front-to-back movement. The carriage frame supports the Delrin block for left/right movement with respect to the frame. Reversible motors are provided to drive the block with respect to the carriage and the carriage with respect to the laser head to position the laser sources and the laser beam lines with respect to the specimen or the opening in the clamping means.

The visible lines produced by the laser beams on the skin of the specimen are focused to have a width of 0.020 inches located about 18 inches from the laser source. Under the typical clamping pressure of about 30 pounds, the breast of the patient would typically space the clamping means from 1 to 3 inches from the supporting platform. The flesh of the specimen tends to bulge upwardly through the opening in the clamping means, making it difficult to fix the location on the skin with the coordinate location of the tumor or lesion as obtained from the X-ray. However, the laser beam line extends to a point adjacent the indicia on the edge of the opening, facilitating the alignment of the laser beam lines with the proper coordinate location.

Once the laser beam lines have been properly located by movement of the carriage with the motor drives, the intersection of the lines is used as the location for inserting the biopsy needle into the skin. Since the needle is about 0.090 inches in diameter, an incision is normally made before inserting the needle. The needle is connected to a source of suction to withdraw a cylindrical core or sample. The angled end of the needle is sharpened but must be rotated as it is inserted to cut the specimen to be removed. It is difficult to maintain the needle in a proper vertical orientation as it is inserted while rotating at the same time. Any deviation from the vertical orientation tends to introduce an error, since the insertion location is predicated on going vertical downwardly to the tumor or lesion location.

The laser beam lines make it possible to accurately maintain the vertical orientation of the biopsy needle as it is inserted. The nature of the laser beam is such that it provides a sharp, well defined line of light at the surface of the specimen and also at a level 10 inches above where the upper end of the biopsy needle terminates. It is therefore possible to use this extended intersection of the laser beams to establish a line along which the biopsy needle must move to properly engage the tumor. After the tip of the needle is located and engaged with the skin, the intersection of the laser beam lines is positioned on the outer end of the needle in an axially aligned location to assure that the needle remains vertical as it is rotated and forced downwardly into the specimen. As long as the axis of the needle is maintained centered on the intersecting beams, the vertical positioning of the needle will be maintained. The fact that the intersection of the beam emanates along the line of the X-ray radiation assures that the biopsy needle will be inserted accurately at the surface of the specimen and will move inwardly to engage the tumor or lesion. As long as the coordinates or the tumor are taken accurately from the X-ray image, the apparatus and method of the present invention provides a completely reliable method of obtaining a biopsy of a tumor or lesion located on an X-ray.

Accordingly, it is an object of the present invention to provide an improved method and apparatus for locating an insertion point and guiding a biopsy needle to engage the tumor or lesion, the location of which has been established by an X-ray.

A further object of the present invention is to provide a laser beam locating and guiding means for use in taking a biopsy of an X-rayed specimen, the means being removably mounted on the X-ray machine between the X-ray head and the specimen.

It is a further object of the present invention to provide an improved laser beam locating and guiding means having laser sources supported by a carriage for movement on two mutually perpendicular axes to produce intersecting lines on a specimen, including means for compensating for carriage movement so that the lines are only shifted laterally.

These and other objects of the invention should be apparent from the following detailed description for carrying out the invention when read in conjunction with the accompanying drawings.

DETAILED DESCRIPTION OF THE PREFERRED EMBODIMENTS

Figure 1:
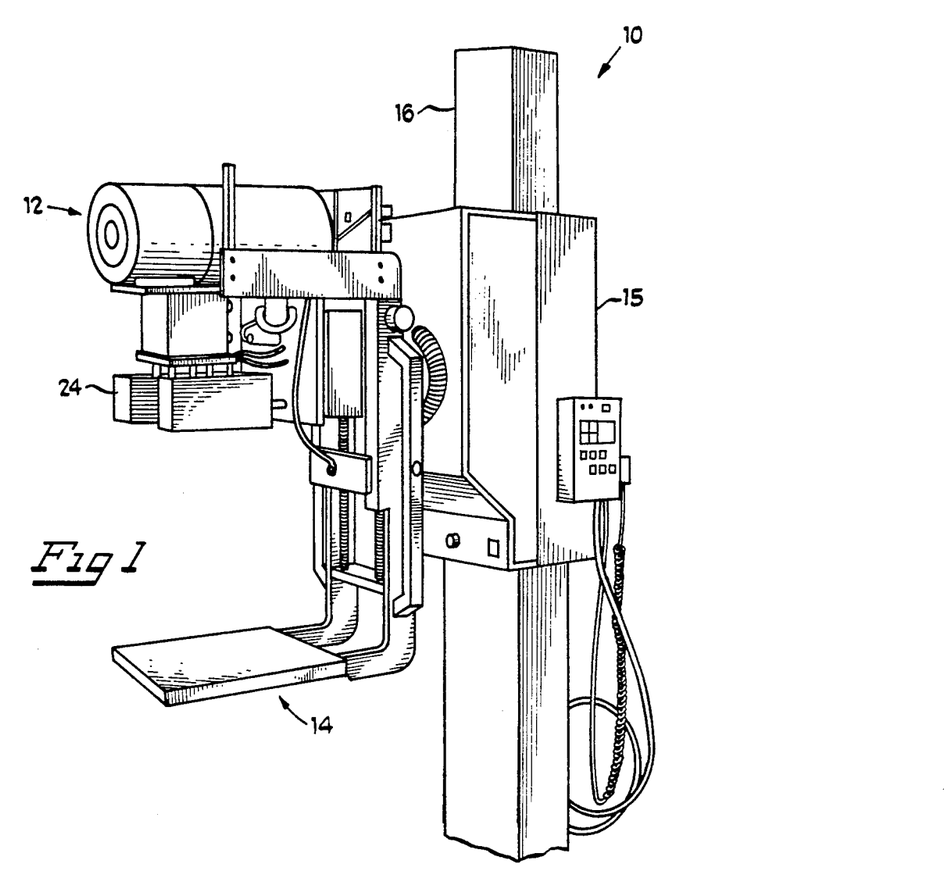
FIG. 1 is a perspective view of an X-ray machine equipped with a laser beam head embodying the present invention.

Referring to FIG. 1 of the drawings, there is shown an X-ray machine 10 which may take the form of any commercially available machine used for diagnostic examinations of the female breast as in mammography. With the recognition of the importance of early detection of cancer in improving the chances of successful treatment, there is increasing use of such X-ray machines in early detection of cancerous tumors or lesions. When such tumors or lesions are noted on X-ray images, it is usually necessary to take a biopsy of the tumor or lesion for further testing to determine the nature of the treatment that should be given to minimize the risk to the patient. Because of the small size of the tumors or lesions in this early detection stage, it is often difficult, time consuming and painful to the patient to obtain the desired biopsy of the tumor or lesion.

The X-ray machine 10 includes an X-ray head 12 from which the X-ray radiation takes place. The radiation is directed toward a support platform 14 which is adjustable in height to support the specimen to be examined, such as a female breast. The machine 10 is provided with a support column 16 and a body portion 15. The platform 14 includes means for disposing the X-ray film beneath the specimen so that when exposed to X-ray radiation from the head 12, an image of the specimen is produced on the film. The illustrated machine 10 is commercially available from Ausonics Corporation of Finland. Manifestly, X-ray machines of other companies may be used with the present invention.

Figure 2:
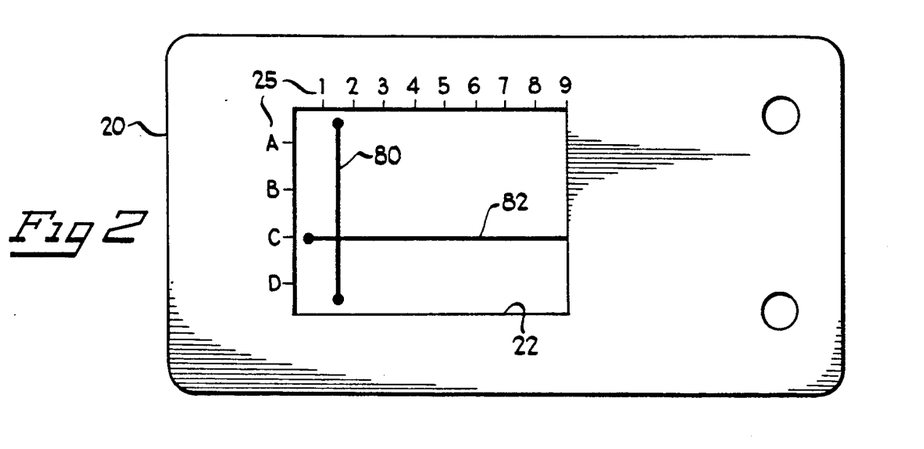
FIG. 2 is a plan view of a clamping plate of the type used in X-ray examination of the female breast.

In order to immobilize and clamp the specimen during the X-ray examination, it is common practice to use paddle or clamping means 20, as shown in FIG. 2. The clamping means 20 is mounted in parallel spaced relation to the support platform 14 and is adapted to apply a pressure of on the order of thirty pounds to the specimen during the initial X-ray examination. The pressure is reduced substantially during the biopsy. In the examination of a female breast, the clamping means 20 would be spaced 2 to 7 cm from the upper surface of the platform 14. To expose a portion of the specimen so that a biopsy may be taken by a biopsy needle 21, the clamping means 20 is formed with a rectangular opening 22. At the edges of the opening 22 there are indicia 24 which permit the designation of locations with the opening 22 by coordinates such as C-1.5, indicating a location aligned with the letter C and the number 1.5. It is known to use such a clamping means provided with this type of indicia to locate a tumor from which a sample is to be taken by a biopsy needle. These clamping means are conventional in the art and need not be described in detail herein. The method and apparatus of the present invention provides a more accurate means of locating such a tumor and performing a biopsy than is now possible with presently known methods and apparatus.

The X-ray machine 10 is provided with means for detachably mounting a laser head 24 immediately below the X-ray head 12 so that the laser beams are radiated substantially along the same axis as the X-rays radiated toward the platform 14.

Figure 6:
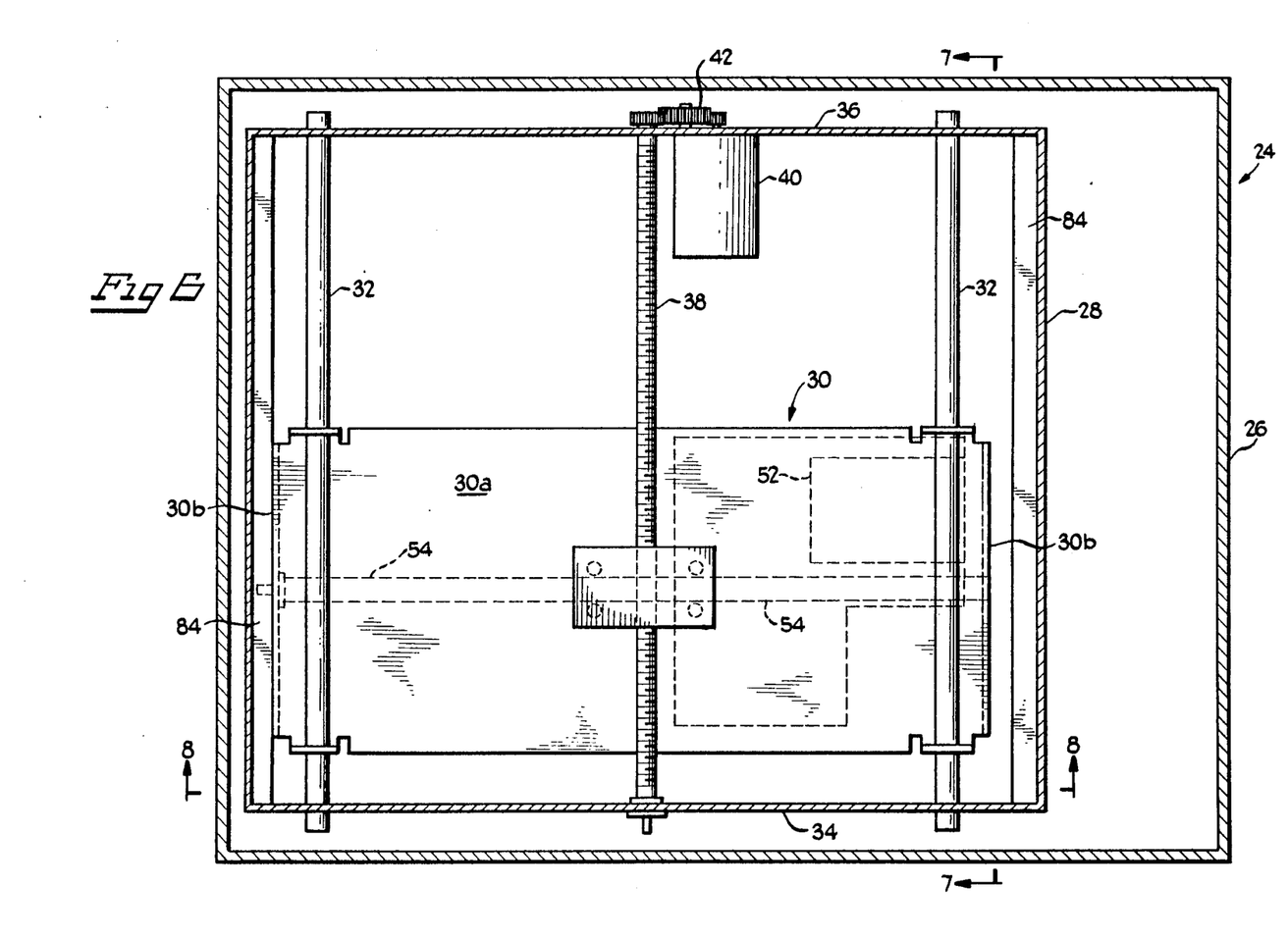
FIG. 6 is a top plan view of the laser head with the top wall cut away for illustrative purposes.
Figure 7:
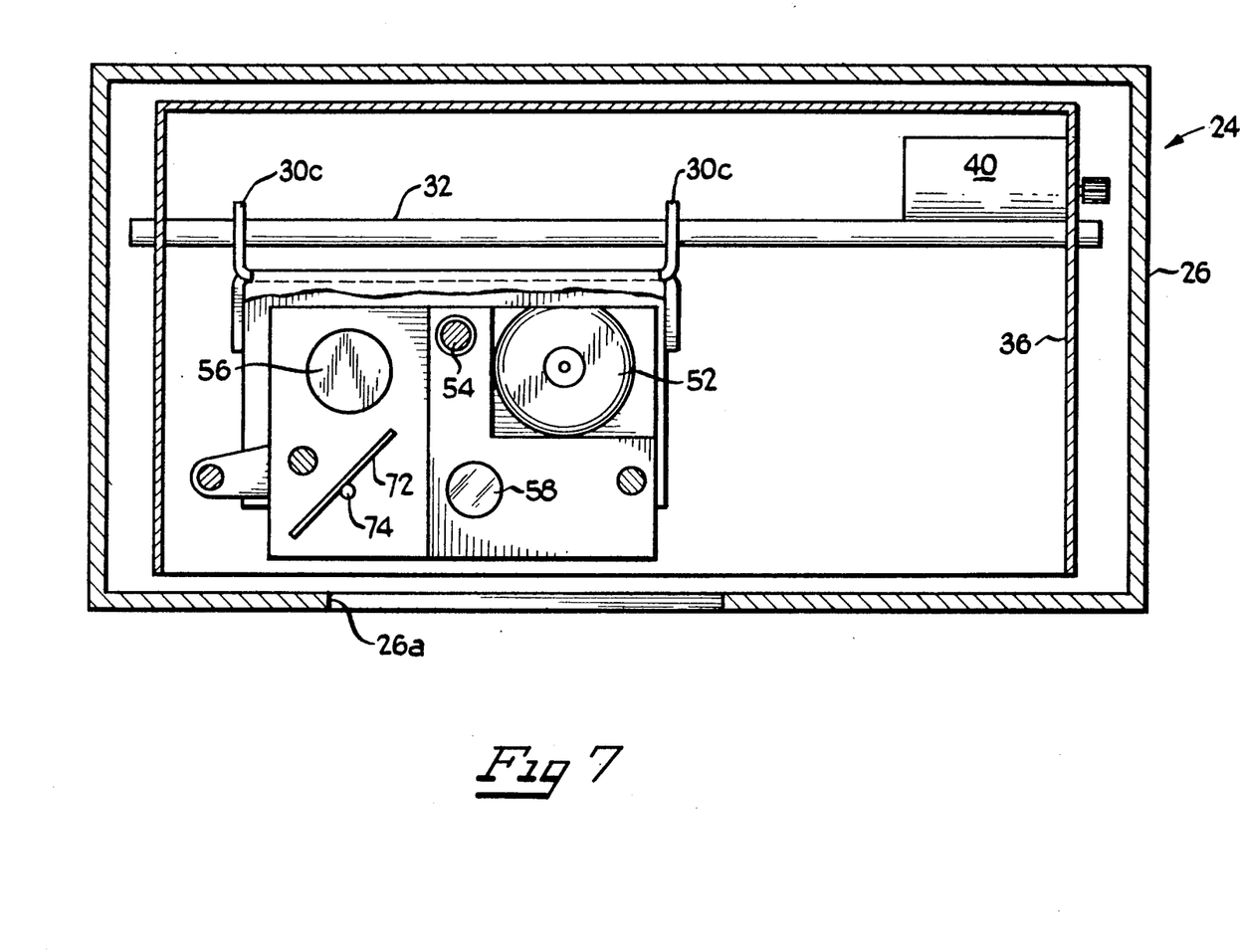
FIG. 7 is a sectional view of the laser head taken on line 7—7 of FIG.6.
Figure 8:
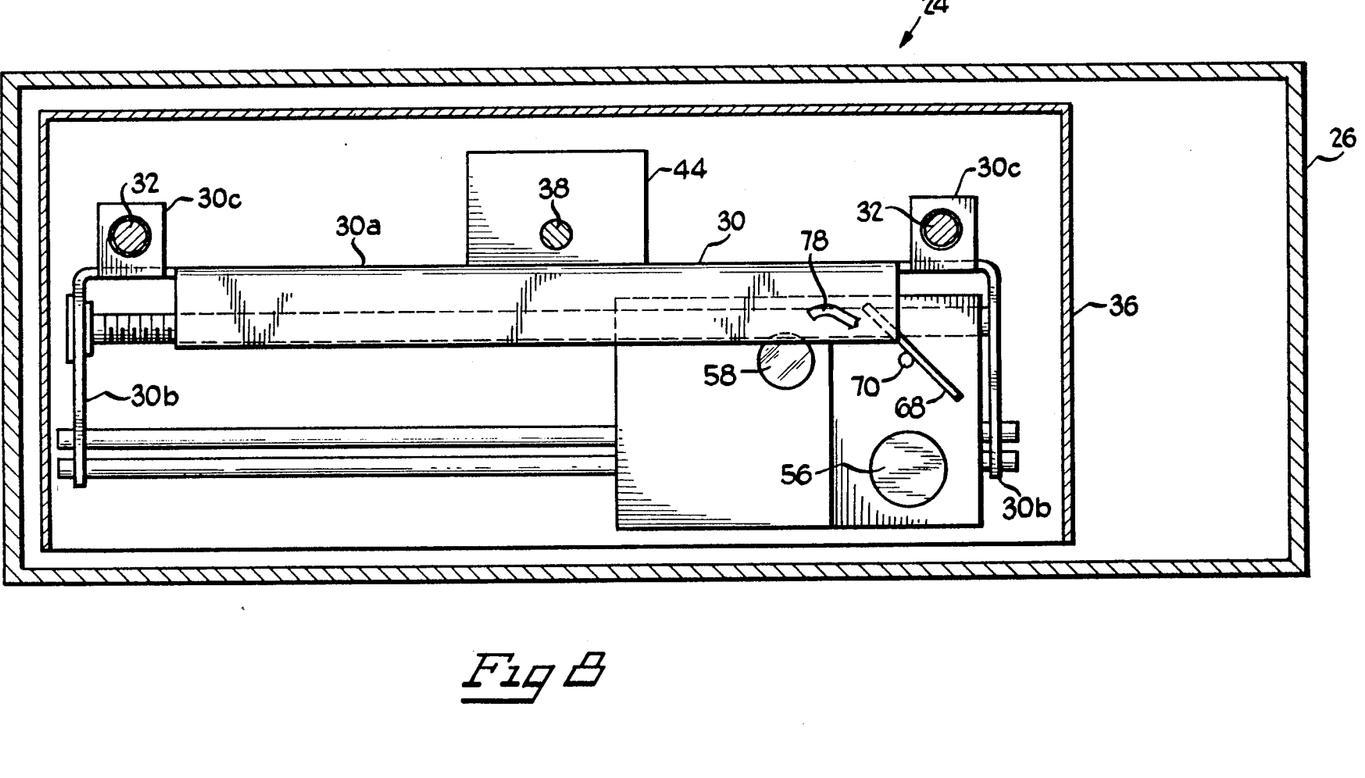
FIG. 8 is a sectional view of the laser head taken on line 8—8 of FIG. 6.

As shown in FIGS. 6-8, the laser head 24 is enclosed in a housing 26 which is closed on all sides except for an opening 26a in its bottom wall, as shown in FIG. 7. The opening 26a is for the purpose of allowing laser beams to be directed from within the housing 26 downwardly onto a specimen on the platform 14. Within the housing 26 there is secured a frame 28 which supports a movable carriage 30. The carriage 30 is supported and guided for horizontal movement by a pair of spaced parallel rods 32 secured to opposed front and back walls 34 and 36 respectively of the frame 28, as shown in FIG. 6.

Figure 3:
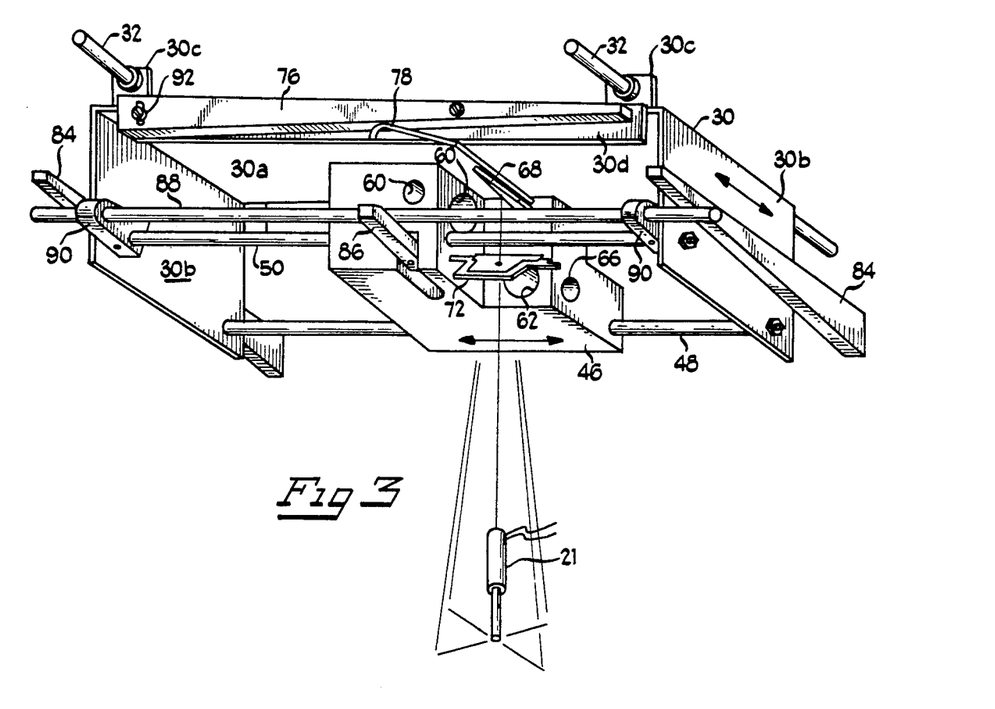
FIG. 3 is a front perspective view from below of the carriage which supports the laser beam sources for the laser beam head.

The carriage 30 is of generally inverted Ushaped configuration having a central portion 30a which extends across beneath the rods 32 and terminates at depending sidewalls 30b. As shown in FIGS. 3 and 8, the carriage 30 is formed with upwardly extending ears or tabs 30c which mount bearings for supporting the carriage for sliding movement along the rods 32. In order to traverse the carriage forwardly and backwardly along the rods 32, a threaded feed screw or shaft 38 is provided between the rods 32 and journaled for rotation in the walls 34 and 36, as shown in FIG. 6. The feed screw 38 is rotated by a reversible motor 40 which drives the screw 38 through an idler gear 42 engaged by spur gears on the motor shaft and the screw shaft 38. At the middle of the carriage 30, there is provided a feed nut 44 which is secured to wall 30a of the carriage and which has a threaded opening to receive the screw shaft 38. Thus, as the screw shaft 38 is rotated by the motor 40, the carriage is caused to traverse along the screw 38 and the rods 32.

Figure 4:
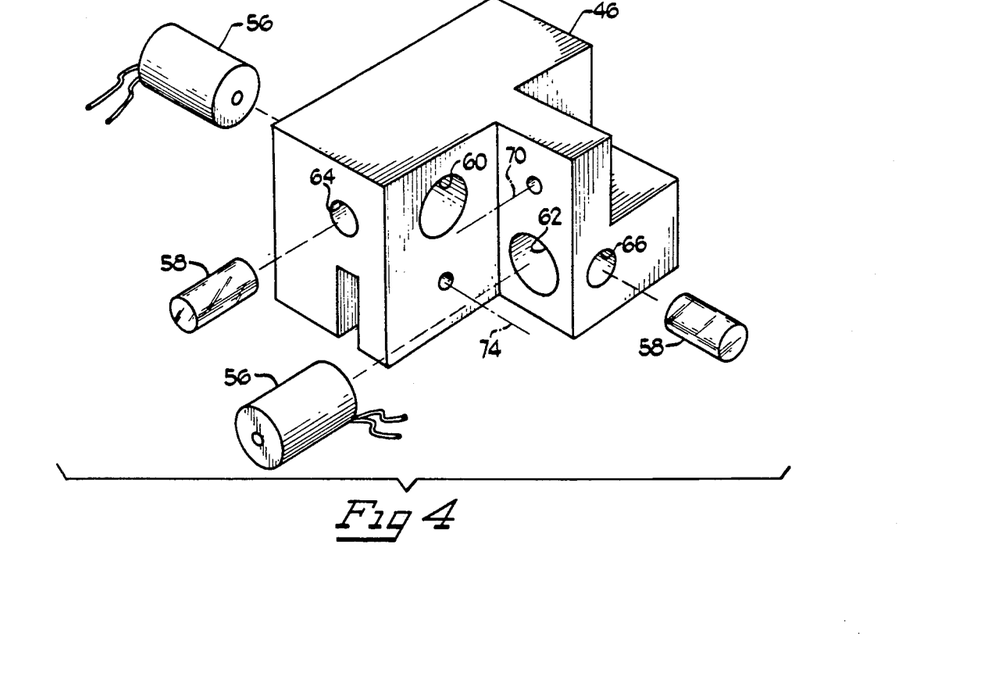
FIG. 4 is an exploded perspective view of the laser diodes and their supporting block.

As is best shown in FIGS. 3 and 4, there is provided a laser support block 46 which is mounted for lateral movement with respect to the carriage 30. The block 46 provides support for the means for generating the laser beams which are used for locating and guiding a biopsy needle as will be explained in detail below. The sidewalls 30b of the carriage 30 fixedly mount the ends of two parallel guide rods 48 and 50 which extend through bored holes in the block 46. The block 46 is preferably machined from Delrin, which is self-lubricating and requires no bearings to mount the block 46 for sliding movement with respect to the rods 48 and 50. As shown in FIG. 7, there is provided a reversible motor 52 mounted on the carriage sidewall 30b to drive a feed screw 54 which engages a feed nut (not shown) on the block 46 in order to drive the block 46 along the rods 48 and 50. An idler gear and spur gears (not shown) drivingly connect the motor 52 to the feed screw 54. From the foregoing, it may be understood that the block 46 is movable laterally with respect to the carriage 30 and that the carriage 30 may traverse forward and back with respect to the mounting frame 28. This arrangement allows the block 46 to be moved front-to-back and side-to-side in a plane parallel to and spaced above the platform 14 and the clamping means 20. The block 46 provides a very inexpensive manner in which to precisely position the lasers and lenses and to maintain their positions despite a considerable handling of the apparatus during its attachment and detachment to the X-ray machine.

Supported within the block 46 are two laser diodes 56 as shown in FIG. 4. The laser diodes 56 are commercially available and are of the type producing an oval beam which may be focused to a line using a cylindrical lens 58. As shown in FIGS. 3 and 4, the block 46 has bored therein two holes 60 and 62 which receive and mount a laser diode 56 in each. Intersecting bored holes 64 and 66 receive and mount the cylindrical lenses 58. The laser diodes 56 are sufficiently recessed within the bored holes 60 and 62 to avoid interference with the lenses 58. The holes 60, 62, 64 and 66 are precision bored to snugly receive the diode lasers 56 and the cylindrical lenses 58 and to position the laser beam generating elements accurately with respect to each other.

Also mounted in the block 46 is a mirror 68 which is disposed at a 45° angle to the uppermost laser beam and which is mounted for pivoted movement about an axis 70 which lies in a vertical plane through the axis of the lowermost laser. Thus, the mirror 68 reflects the narrow beam downwardly in a vertical plane which intersects the vertical plane including the other laser beam.

Located immediately below the mirror 68 is a beam splitter 72 which will reflect 50% of the beam impinging on its surface and will pass through 50% of the beam. The beam splitter 72 is mounted for rotation about an axis 74 and is disposed at a 45° angle to the downwardly directed beam from the uppermost laser and at a 45° angle to the lowermost laser which is directed horizontally into the beam splitter 72. As a result, the beam splitter produces a downwardly directed beam which is the combination of 50% of the reflected beam from the lowermost laser and the 50% of the beam passed through from the uppermost laser. The two downwardly directed beams are intersecting and produce cross lines at the specimen or in the opening 22 in the clamping means 20.

Figure 5:
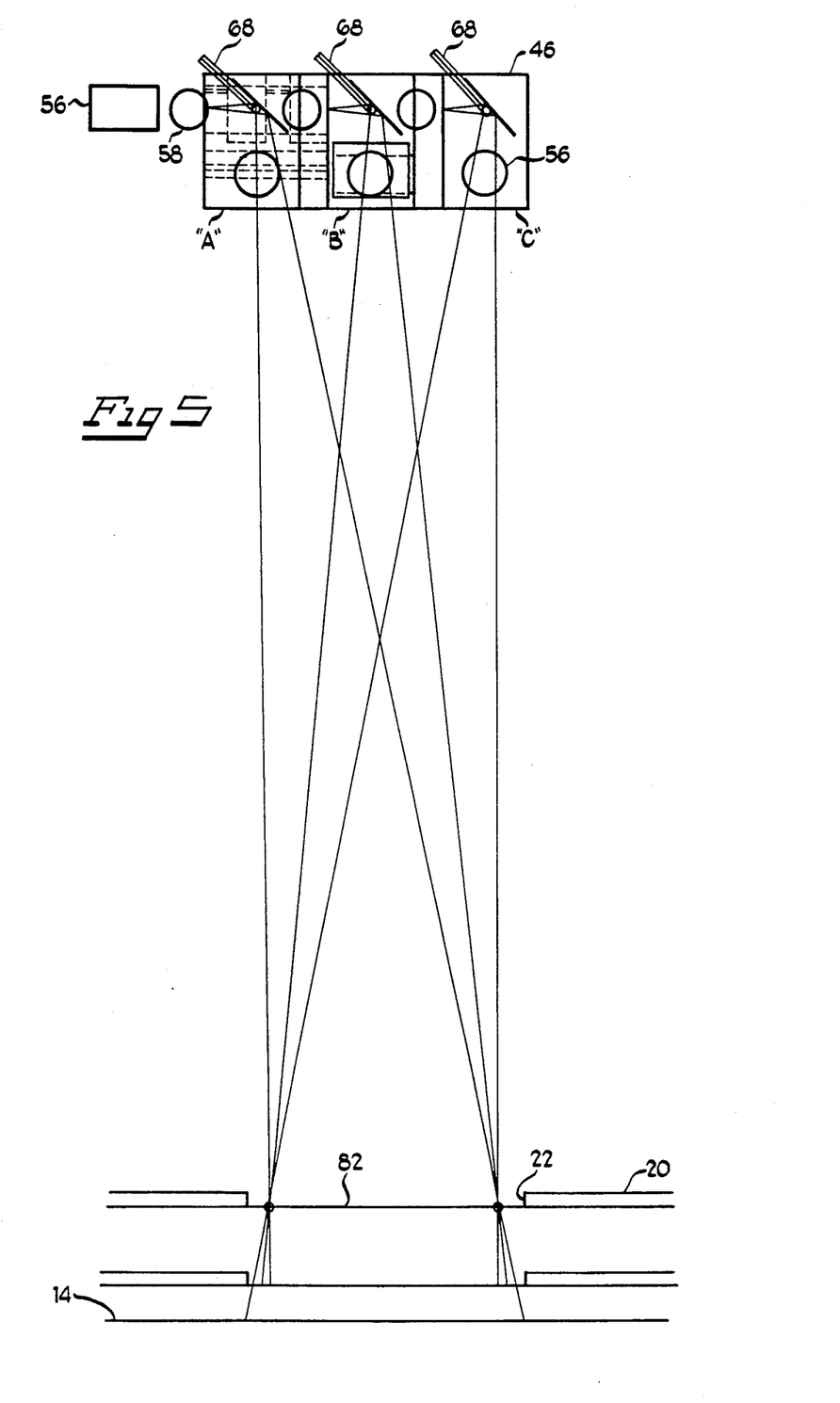
FIG. 5 is a diagrammatic view of the laser beam source in various positions illustrating the compensating mirror movement to maintain the image position fixed.

As explained above, it is important to maintain the laser beam line within the opening 22 on the clamping means 20, since reflections of the laser beam from the surface of the clamping means is very distracting and objectionable. Accordingly, means are provided in the laser head 24 to compensate for the traversing of the carriage 30 or the block 46 by adjusting the mirror 68 or the beam splitter 72 so that the laser beam lines stay within the opening 22. The problem of eliminating such reflections is complicated by the fact that the clamping means may be positioned different distances from the platform 14 depending on the thickness of the specimen when it is compressed by the clamping means 20. As noted above, this thickness may vary from 2 to 7 cm, or a total variation of about 2 inches. FIG. 5 shows how the spread or divergence of the laser beam increases in this 2 inch space and how the traversing of the carriage 30 to position the laser beam lines in the opening 22 increases the clearance that must be provided at the uppermost position of the clamping means 20. Thus, the relative positions of the laser diodes 56 and lenses 58 are selected so that the laser beam lines are slightly less in length than the length and width of the opening 22 in the clamping means 20.

Referring to FIG. 3, there is shown the compensating means for the mirror 68 which includes a laterally extending sloping cam 76 which is secured to a wall 30d of the carriage 30. A cam follower 78 extends from the mirror 68 and serves to rotate the mirror 68 about its mounting axis 70 as the block traverses laterally with respect to the carriage 30. This rotation of mirror 68 movement thus causes the right-to-left extending line to stay within the opening 22 as the front-to-back line is moved across the specimen or target area. This action of the cam 76 and follower 78 is best illustrated by reference to FIG. 5.

Shown diagrammatically is a portion of block 46 supporting mirror 68 in three different positions, illustrating how the mirror adjusts the beam as the block 46 traverses laterally to reposition the other (front-to-back) beam. In the position designated as "B" in FIG. 5, the block 46 is centrally located with respect to the carriage 30, positioning line 80 in FIG. 2 at the "5" mark or in the center of the left-to-right scale. In the "A" and "C" positions shown in FIG. 5, the block has traversed to the left and right, respectively. The action of the cam follower 78 on the cam 76 causes the right-to-left line 82, as shown in FIGS. 2 and 5, to remain within the opening 22. In the position "A" from FIG. 5, the line 80 (front-to-back) would be to the left edge of the opening 22, as shown in FIG. 2.

The compensation means for the beam splitter 72 is similar to that provided for the mirror 68. A pair of cams 84 are mounted on the inside walls of the frame 28, as shown in FIGS. 3 and 6, and extend in parallel spaced relation to the sidewalls 30b of the carriage 30. Coupled to the beam splitter 72 along the pivot axis 74 is a cam follower lever 86 which is engaged with a cam follower bar 88, as shown in FIG. 3. The bar 88 is supported for swinging movement against the underside of the cams 84 by links 90. Thus, as the carriage 30 traverses front-to-back, the bar 88 rides against the cams 84, causing the cam follower lever 86 to rotate the beam splitter 72. This action of the cams and cam follower lever causes the front-to-back line 80 to be adjusted or redirected as the carriage 30 traverses to move the right-to-left line 82 toward the front or back of the opening 22. In this manner the line 80 is maintained within the opening and does not engage the clamping means 20, causing objectionable reflections.

It may be necessary on some occasions, such as during initial set-up of the X-ray machine and attachment of this invention thereto, to initially center the lines 80 and 82 within the opening 22 of the clamping means 20. For this purpose, there are provided externally accessible adjustment means for the cams 76 and 84. Suitable positioning of these cams can be used to properly position the lines 80 and 82 within opening 22. In FIG. 3 there is shown an adjustment means 92 for the cam 76 as an example.

Figure 9:
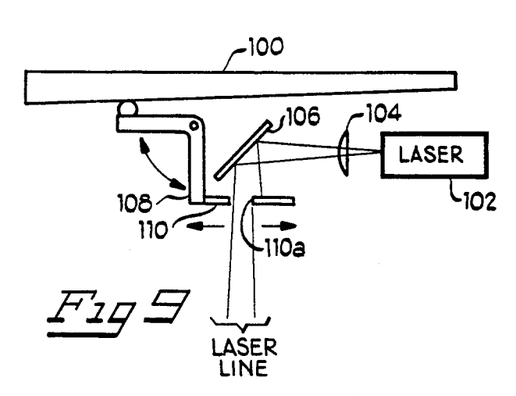
FIG. 9 is a diagrammatic view of an alternative embodiment of the invention.
Figure 10A:
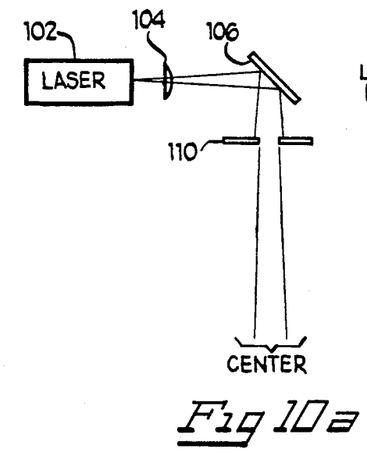
FIGS. 10a, 10b and 10c are schematic diagrams of the action of the laser beam control by the alternative embodiment of FIG. 9.
Figure 10B:
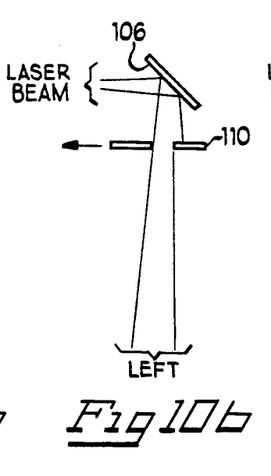
Figure 10C:
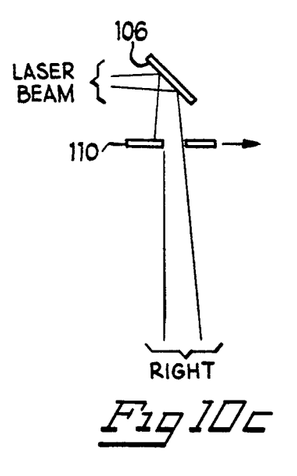

Shown in FIG. 9 is an alternative embodiment of the invention wherein the compensating means for directing the laser beams during traversing of the laser beam sources constitutes movable shutters, rather than the pivotal movement of the mirror and beam splitter. As shown in FIG. 9, a cam 100 is positioned adjacent the carriage which supports a laser diode 102, a lens 104, a mirror 106 and a cam follower 108. A shutter 110 is mounted on the carriage beneath the mirror 106 for movement in the plane of the carriage movement along a path aligned with the plane of the laser beam. The shutter 110 has an opening 110a through which the beam is directed and which functions to define the length and position of the beam passing therethrough. As shown in FIGS. 10a, 10b and 10c, the shutter 110 functions in the same manner as the pivoting mirror in compensating for the carriage movement to maintain the laser beam within the target area.

A second shutter would be utilized in the alternative embodiment to compensate for the movement of the beam in the orthogonal direction also. Thus, there are two separate shutters and cams controlling the displacement of both of the laser beams as in connection with the embodiment of FIGS. 3-8. The laser diode 102 and lens 104 provide a beam of sufficient width to completely span the opening 22 in the clamping means 20 at the limits to which the carriage may traverse. By movement of the shutter 110 by the action of the cam 100, the shutter 110 effectively cuts off the ends of the laser beam line which would otherwise extend beyond the edges of opening 22 as a consequence of the displacement of the carriage from its central location. The other laser beam would similarly have the edges of its beam limited by the cams that had controlled the angling of the beam splitter. Either the shutter or the pivotal mirrors provide an acceptable means for limiting the laser beams to the target area within the opening 22 of the clamping means.

In the normal use of the laser head 24 and in the practice of the method of the present invention, an X-ray picture is utilized to establish the location of a tumor or lesion which is to be the subject of a biopsy. Through the use of a scale, the coordinates locating the tumor on the X-ray picture are established. Through the operation of the motors 40 and 52, the laser beam lines 80 and 82 are moved within the opening 22 to position the lines in accordance with the measured coordinates. This provides the precise location on the skin where the biopsy needle should be inserted. The two laser beams provide sharp, distinct lines which are 0.020 inch in width and may be easily seen with any ambient light conditions in the area of the X-ray equipment. The point of the intersection of the lines is created by laser beam portions projecting vertically with respect to the specimen being examined, so any bulging of the flesh through the opening in the clamping means has no tendency to introduce errors in the location of the surface point above the tumor.

Even if the surface location is toward the edge or corner of the opening 22, the intersecting beam will still be vertical and the ends of the laser beam lines will still be within the opening 22. Thus, there will be no objectionable reflections caused by the laser beams reflecting on the clamping means 20. Having established the location on the skin surface with the laser beam lines, an incision is made at the indicated location which has not been contaminated by the need to mark the skin to locate the tumor. The biopsy needle is then inserted at the point marked by the laser beam lines. Herein, the intersection line of the focused beams is on a true vertical line through the X-ray head of the machine. By aligning the biopsy needle on this true vertical, the lower tip of the needle will progress straight down to the lesion and not go off to the side of the lesion as occurs when the needle is tilted to the true vertical. The vertical orientation of the needle is continually maintained so that the laser beam lines intersect and provide a cross with a central dot at the cross section on the upper end of the needle, along the needle axis. By maintaining the dot centered on the upper end of the needle as the needle is rotated in taking the biopsy sample, the vertical positioning of the needle is assured. Having accurately established the skin location for inserting the biopsy needle and having maintained the vertical orientation of the needle, the operator has improved considerably the likelihood of properly engaging the tumor for biopsy on the first attempt, as compared to the prior art methods which were less precise.

From the foregoing description, it should be readily understood that the present invention provides a significant improvement in the method and apparatus for performing a biopsy on a tumor or lesion which has been identified and located by means of an X-ray. The laser beam lines generated by the laser head 24 provide a means of using a coordinate location as determined from an X-ray picture to accurately establish a location on the skin of the specimen for inserting a biopsy needle, and thereafter using the laser beam lines to maintain the vertical positioning of the biopsy needle while rotating the needle and forcing it into the specimen. By centering the axis of the needle on the intersecting laser beam lines, the needle will be properly directed to engage the tumor or lesion.

Although the invention has been described with regard to various preferred embodiments, it should be understood that various changes and modifications as would be obvious to one having the ordinary skill in this art may be made without departing from the scope of the invention which is defined in the appended claims.

What is claimed is:

1. A laser device for attachment to an apparatus for providing pictures of a target area in a person, said laser device comprising:

a laser head including a first laser source radiating a focused beam in a first plane and visible as a first line in the target area, a second laser source radiating a focused beam in a second plane and visible as a second line in said target area, said second plane intersecting said first plane at an angle, said focused beams being in an intersecting relationship from said head to said target area;

a moveable carriage in the laser head moveable in a first direction and carrying both the first laser source and the second laser source together for movement in a first direction;

a moveable support means in the carriage for supporting both the first laser source and the second laser source for travel together relative to said carriage in a second direction orthogonal to said first direction;

means for moving the carriage and the support means in the orthogonal directions and thereby moving said first laser source perpendicular to said first line and for moving said second laser source perpendicular to said second line; and means for directing said focused beams emanating from the laser sources toward the lesion and directing their intersection as a cross line for marking an insertion location for a biopsy needle in said target area and providing an intersecting line from said insertion location to align the needle during insertion to the lesion.

2. A device for locating and guiding a biopsy needle in accordance with claim 1 including means for mounting said first and second laser sources in said laser head at locations fixed with respect to each other and for radiating said beams to intersect and form the intersecting line, said means for directing including a mirror reflecting radiation from said first laser source toward said target area, and including a beam splitter positioned on said axis to reflect said radiation from said second laser source toward said target area, said radiation from said first laser source passing through said beam splitter to provide intersecting beams projectable as the cross line.

3. A device for locating and guiding a biopsy needle in accordance with claim 2 wherein said mirror and said beam splitter are pivoted about axes fixed with respect to each other, and compensating means for pivoting said mirror and said beam splitter as said moveable carriage and moveable support means moves said focused beams.

4. A device for locating and guiding a biopsy needle in accordance with claim 3 wherein said first and second laser sources are mounted on said moveable carriage which is moveable in a plane parallel to said target area in two orthogonal directions, said compensating means comprising cam means positioned adjacent to said carriage and extending in the two directions of orthogonal movement, said compensating means further comprising cam followers secured to said mirror and beam splitter and engaging said cam means to rotate said mirror and beam splitter in accordance with the movement of said carriage.

5. Apparatus for use in X-ray examination and diagnostic procedures comprising:

an X-ray machine having an X-ray radiation head mounted in spaced relation to a patient and specimen supporting platform for supporting a specimen, a clamping means mounted in spaced parallel relation to said platform to clamp the specimen against said platform and against movement relative to the X-ray machine, said clamping means having an opening exposing a portion of the specimen;

indicia associated with the clamping means for locating a lesion on an X-ray picture by means of coordinates showing in the X-ray pictures taken by the X-ray radiation head;

a laser head detachably supported on said X-ray machine between said X-ray radiation head and the specimen supporting platform;

first and second laser sources mounted in said laser head and radiating focused beams in first and second planes intersecting along an intersecting line and providing cross lines intersecting on said portion of the specimen and lying within said opening;

means for moving the laser head to shift the laser head and the cross lines to a position in accordance with the coordinates location of the lesion as shown by the X-ray picture; and a biopsy needle having a hollow sharpened end at one end for insertion into the specimen to remove a core sample of the specimen, said needle at the other end receiving the cross lines which appear as a dot on the other end of the needle for locating the axis of said needle with respect to said specimen during insertion of the needle for removal of said core sample.

6. Apparatus for use in X-ray examination and diagnostic procedures in accordance with claim 5 wherein the X-ray radiation from said X-ray radiation head to the exposed portion of said specimen is substantially along the the intersecting line extending to said first and second laser sources.

7. Apparatus for use in X-ray examination and diagnostic procedures in accordance with claim 6 wherein said first and second laser sources are supported on a carriage movable in two orthogonal directions in a plane parallel to said platform, said cross lines formed by beams are perpendicular, said carriage being movable in directions parallel to each of said lines.

8. Apparatus for use in X-ray examination and diagonistic procedures in accordance with claim 7 wherein said opening in said clamping plate is rectangular having sides extending parallel to said lines defined by said beams, said indicia being located on said clamping plate along the sides of said opening for providing the coordinates for use in correlating biopsy samples with lesion locations as shown in X-rays.

9. Apparatus for use in X-ray examination and diagnostic procedures in accordance with claim 8 including means for redirecting said beams as said carriage is moved in either of said two directions.

10. Apparatus for use in X-ray examination and diagnostic procedures in accordance with claim 9 wherein means for redirecting said beams includes orthogonally disposed cams each of which extends in one of the directions of carriage movement and controls the direction of radiation of one of said laser sources in dependence on the position of the carriage in its movement.

11. A method of locating and obtaining a biopsy of a lesion in a specimen comprising:

clamping a specimen with clamping means in a fixed position in an X-ray machine;

radiating the specimen with X-rays to form an X-ray picture of the specimen to locate a lesion;

providing indicia means associated with the clamping means for locating a lesion on said X-ray picture by means of coordinates;

noting the coordinates for the lesion from the indicia means;

generating laser beams to provide two laser beams focused as intersecting planes emanating from a location along the line of the X-ray radiation;

moving and positioning the laser beam at the respective coordinate positions on the clamping means and in accordance with the coordinate locations of said lesions as shown by the X-ray picture;

applying the tip of a biopsy needle to the intersection on the specimen of the planes formed by the laser beams; and orienting the biopsy needle while inserting it into the specimen using the intersection of the laser beam planes to maintain the orientation of said needle at the lesion coordinates the taking a biopsy sample of the lesion.

12. Apparatus for locating and guiding a biopsy needle in relationship to a breast immobilizing framework comprising:
- a breast supporting platform, including a clamping means having an opening through which access may be had to a breast clamped to said platform;
- a frame;
- an X-ray device providing a source of X-rays mounted on said frame in spaced relation to said platform to radiate a breast supported on said platform to provide an X-ray picture of a lesion in a breast;
- indicia associated with the opening in the clamping means and providing on the X-ray picture orthogonal coordinates to locate a lesion;
- a laser head detachably mounted on said frame between said source of X-rays and said platform, said head including a first laser source radiating a focused beam in a first plane visible as a first line on said breast, a second laser source radiating a focused beam in a second plane visible as a second line on said breast and intersecting said line from said first laser source at 90°;
- translating means for moving said first laser source perpendicular to said first line and for moving said second laser source perpendicular to said second line and to the coordinates for the lesion as seen in the X-ray picture; and
- the intersection of said beams from said first and second laser beams providing a line aligned along a travel path of X-rays from the X-ray source to the lesion for locating a needle insertion point and maintaining said needle aligned with the lesion.

* * * * *

UNITED STATES PATENT AND TRADEMARK OFFICE
CERTIFICATE OF CORRECTION

PATENT NO. : 5,316,014
DATED : May 31, 1994
INVENTOR(S) : Livingston

It is certified that error appears in the above-indentified patent and that said Letters Patent is hereby corrected as shown below:

Column 12, line 13, after "the" delete --the--.

Column 12, line 57, change "beam" to --beams--.

Column 12, line 67, after "coordinates" change "the" to --and--.

Signed and Sealed this

Eleventh Day of October, 1994

Attest:

BRUCE LEHMAN

*Attesting Officer*  *Commissioner of Patents and Trademarks*